United States Patent
Corbeil et al.

(10) Patent No.: US 8,630,693 B2
(45) Date of Patent: Jan. 14, 2014

(54) MAGNETIC RESONANCE DEVICE HAVING A PET UNIT

(75) Inventors: James Corbeil, Knoxville, TN (US); Stefan Stocker, Grossenseebach (DE)

(73) Assignee: Siemens Aktiengesellschaft, Munich (DE)

(*) Notice: Subject to any disclaimer, the term of this patent is extended or adjusted under 35 U.S.C. 154(b) by 267 days.

(21) Appl. No.: 12/379,812

(22) Filed: Mar. 2, 2009

(65) Prior Publication Data
US 2009/0221903 A1 Sep. 3, 2009

(30) Foreign Application Priority Data
Mar. 3, 2008 (DE) .................. 10 2008 012 312

(51) Int. Cl.
*A61B 5/055* (2006.01)
(52) U.S. Cl.
USPC ........... 600/411; 600/410; 600/415; 600/422; 600/436; 324/318; 324/321; 250/363.04
(58) Field of Classification Search
USPC .......... 600/410, 411, 415, 422, 436; 324/318, 324/321; 250/363.04
See application file for complete search history.

(56) References Cited

U.S. PATENT DOCUMENTS

| | | | | |
|---|---|---|---|---|
| 6,060,883 A | * | 5/2000 | Knuttel | 600/422 |
| 2004/0158922 A1 | * | 8/2004 | Eberler et al. | 5/81.1 R |
| 2005/0113667 A1 | * | 5/2005 | Schlyer et al. | 600/411 |
| 2006/0241386 A1 | * | 10/2006 | Yanagita et al. | 600/415 |
| 2006/0261813 A1 | * | 11/2006 | Schuster et al. | 324/318 |
| 2007/0116546 A1 | * | 5/2007 | Dearing | 414/482 |

FOREIGN PATENT DOCUMENTS

| | | |
|---|---|---|
| DE | 102006037047 A1 | 2/2008 |
| DE | 102006045427 A1 | 4/2008 |
| DE | 102006054542 A1 | 6/2008 |
| DE | 102007009180 A1 | 8/2008 |
| WO | WO 2006119085 A2 * | 11/2006 |

* cited by examiner

*Primary Examiner* — Unsu Jung
*Assistant Examiner* — Phong K Huynh
(74) *Attorney, Agent, or Firm* — Harness, Dickey & Pierce, P.L.C.

(57) ABSTRACT

In a magnetic resonance device having a PET unit for acquiring positron emission tomography data and a gradient coil, the PET unit includes a carrier tube on which at least one PET detector is arranged. In at least one embodiment, the carrier tube is arranged inside the gradient coil and is displaceably mounted in such a way that access to the PET detector is made possible by its displacement. This allows easy access to the PET detector during maintenance activities.

13 Claims, 3 Drawing Sheets

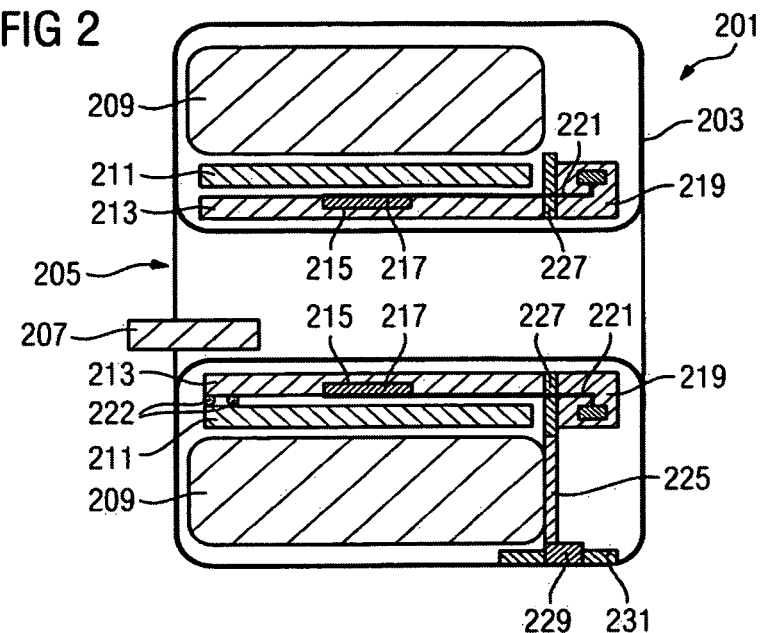
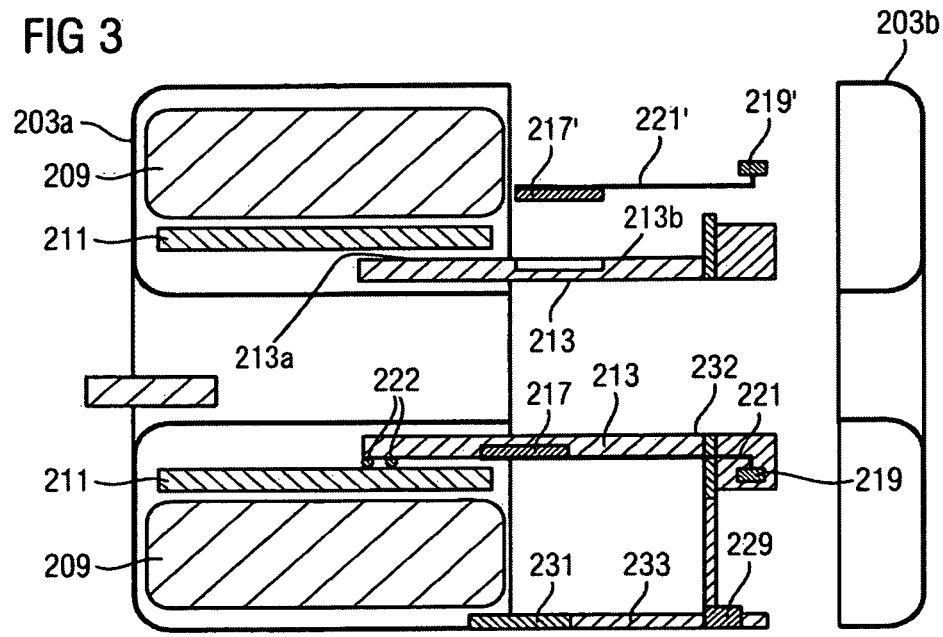

MAGNETIC RESONANCE DEVICE HAVING A PET UNIT

PRIORITY STATEMENT

The present application hereby claims priority under 35 U.S.C. §119 on German patent application number DE 10 2008 012 312.9 filed Mar. 3, 2008, the entire contents of which is hereby incorporated herein by reference.

FIELD

At least one embodiment of the present invention generally relates to a magnetic resonance device having a PET unit. In at least one embodiment, the PET unit is for acquiring positron emission tomography data and the magnetic resonance device includes a gradient coil. Further, the PET unit includes a carrier tube on which at least one PET detector is arranged and the carrier tube is arranged inside the gradient coil.

BACKGROUND

Positron emission tomography (PET) has become increasingly widely established in the medical diagnostics field in the last several years in addition to magnetic resonance tomography (MR). Whereas MR is an imaging method for representing structures and slice images in the interior of the body, PET enables a visualization and quantification of metabolic activities in vivo.

PET exploits the special properties of positron emitters and positron annihilation for quantitatively determining the functioning of organs or cell regions. For this purpose suitable radiopharmaceuticals labeled with radionuclides are administered to the patient prior to the examination. Upon decaying, the radionuclides emit positrons which after a short distance interact with an electron, thereby resulting in the occurrence of a so-called annihilation. During this process two gamma quanta are generated which fly apart in opposite directions (offset by 180°). The gamma quanta are detected within a specific time window by two oppositely disposed PET detector modules (coincidence measurement), as a result of which the site of the annihilation is pinpointed to a position on the connecting line between the two PET detector modules.

For detection purposes the PET detector module must generally cover a major part of the length of the gantry. The module is subdivided into detector elements having a side length of a few millimeters. Upon detecting a gamma quantum each PET detector element generates an event record which indicates the time and the detection site, that is to say identifies the corresponding detector element. This information is transferred to a fast logic circuit and compared. If two events coincide within a maximum specified time interval a gamma decay process is assumed to have occurred on the connecting line between the two associated PET detector elements. The PET image is reconstructed by way of a tomography algorithm, referred to as back-projection.

It is advantageous to allow MR and PET examinations simultaneously within one device. In this case both morphological MR data and PET data can be acquired within one measurement pass. For this purpose it is necessary to arrange the PET detectors inside the MR device such that the imaging volumes ideally coincide. For example, the PET detectors can be arranged on a supporting structure (carrier tube, gantry) located inside the MR device. These can be, for example, 60 detectors in an annular arrangement on the carrier tube. A cooling terminal and electric supply leads are required for each of the detectors, which can also be combined into detector blocks. These also have to be arranged in the MR device. In addition a number of signal processing units are required which are likewise arranged in the MR device. These are connected to the detectors by way of the electric supply leads and are used for signal processing.

Frequent maintenance interventions are necessary on the PET detectors as well as on the signal processing units. In this case the affected units and detectors may need to be replaced or must be removable and accessible for repair purposes. In maintenance activities of the kind any impact on the remaining device, particularly on the unaffected PET detectors and signal processing units, should be avoided as far as is practically possible.

SUMMARY

In at least one embodiment of the present invention, a magnetic resonance device includes a PET unit wherein maintenance interventions can be performed on the PET unit in a easy manner.

The magnetic resonance device according to one embodiment of the invention includes a PET unit for acquiring magnetic resonance data and positron emission tomography data. It further includes a magnet and a gradient coil, the PET unit including a carrier tube on which at least one PET detector is arranged and the carrier tube being arranged inside the gradient coil. The carrier tube is displaceably mounted within the magnetic resonance device in such a way that access to the PET detector is made possible by its displacement. The displaceable mounting of the carrier tube enables maintenance to be carried out on the PET detector without the need to disassemble the magnetic resonance device. In particular it is thus possible to reduce the necessary maintenance time and increase reproducibility. Complicated and time-consuming calibration following a maintenance activity can be largely avoided.

In an advantageous embodiment of the invention at least one sliding bearing is arranged between the gradient coil and the carrier tube. The bearing provided is a simple way of implementing the displacement of the carrier tube. During the displacement a guiding of the carrier tube is simultaneously realized, such that on completion of the maintenance the carrier tube returns once again to its home position. By this, it is ensured that the maintained PET detectors return to their original position.

In an advantageous embodiment of the invention the magnetic resonance device includes a sliding rail which is connected via a supporting element to an end of the carrier tube which exits the magnetic resonance device during displacement. An additional guiding of the carrier tube during the displacement is implemented thereby. In particular the forces acting on the bearing located inside the magnetic resonance device are reduced as a result of the support.

An embodiment of the invention of the type wherein the running rail has a junction point for accommodating an extension into which the supporting element can be transferred during displacement of the carrier tube is advantageous. This enables the running rail to be implemented with a comparatively short length, such that it is contained completely within the magnetic resonance device during normal operation. Only in the event of maintenance will the magnetic resonance device be opened, the extension installed and the carrier tube removed at least partially from the magnetic resonance device by displacement.

In an advantageous embodiment of the invention the magnetic resonance device includes at least one processing unit for PET signals which is disposed on the carrier tube and arranged at the end of the carrier tube exiting the magnetic resonance device during displacement. The processing unit is preferably not arranged inside the magnet and the gradient coil so that fewer requirements in terms of a smallest possible implementation have to be imposed in the course of choosing the design. Parts of the magnetic resonance device that are located inside the gradient coil should be implemented as small in order to maximize the diameter of the patient opening.

In an advantageous embodiment variant of the invention the magnetic resonance device includes an enclosure comprising at least two enclosure parts, the enclosure parts being detachably connected to each other and embodied in such a way that a displacement of the carrier tube is made possible when a first enclosure part is removed. By way of the removable enclosure part it is possible to conceal elements located at the end of the carrier tube, such as the processing unit and the running rail, when the magnetic resonance device is in the operating state. If maintenance is necessary, the enclosure part can easily be removed and the carrier tube pushed out of the magnetic resonance device.

An embodiment of the invention is advantageous wherein an excitation coil is arranged between the carrier tube and the gradient coil in such a way that it is displaceable together with the carrier tube.

A magnetic resonance device in at least one embodiment includes a shielding for high-frequency radiation, arranged on the inside of the carrier tube in such a way that it can be displaced together with the carrier tube.

BRIEF DESCRIPTION OF THE DRAWINGS

Further advantages and embodiments of the invention will emerge from the example embodiments described below in connection with the figures, in which:

FIG. 2 shows an example embodiment variant of the invention in the operationally ready state, FIG. 3 shows the embodiment variant of the invention during a maintenance intervention.

DETAILED DESCRIPTION OF THE EXAMPLE EMBODIMENTS

Figure 1:
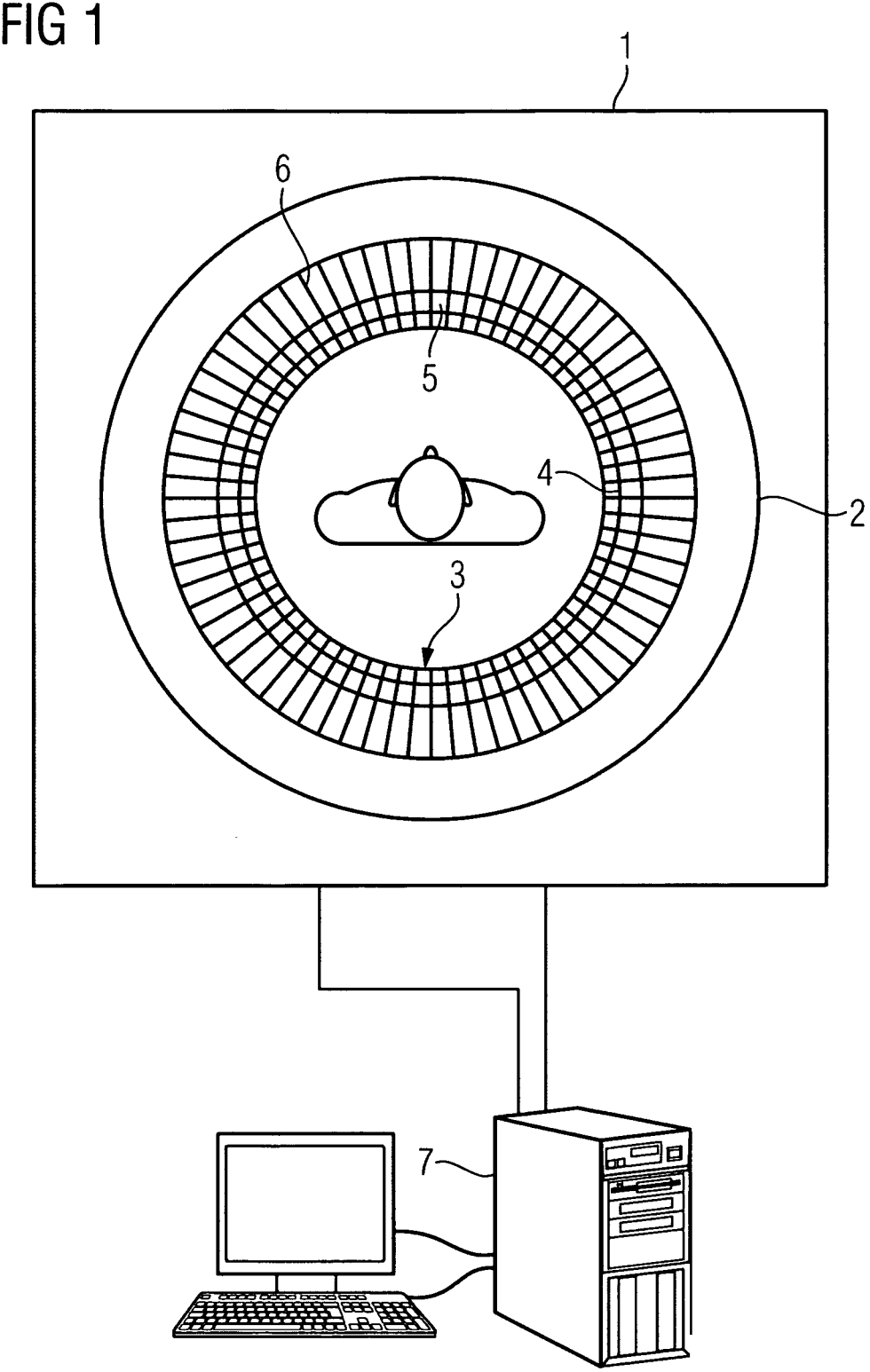
FIG. 1 shows a schematic representation of an MR/PET combination device.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The example embodiments of the invention can preferably be used on a combined MR/PET device. A combined device has the advantage that both MR and PET data can be acquired isocentrically. This enables the examination volume within the region of interest to be precisely defined by way of the data of the first modality (PET) and the information to be used in the further modality (e.g. magnetic resonance). Although it is possible to transfer the volume information of the region of interest from an external PET device to an MR device, this entails increased overhead in terms of the registering of the data.

In general all data determinable using magnetic resonance or other imaging methods can be acquired at the region of interest selected on the PET dataset. Instead of the spectroscopy data, for example, fMR data, diffusion maps, T1- or T2-weighted images or quantitative parameter maps can also be acquired by way of magnetic resonance examinations in the region of interest. Equally, computed tomography methods (e.g. perfusion measurement, multi-energy imaging) or X-ray imaging can be used. An advantageous aspect of the described method is that the region of interest can in each case be restricted in a very specific manner by way of the PET dataset to a particular pathology that is present in the patient.

In addition, however, it is also possible, by using a plurality of so-called tracers, to represent different biological characteristics in the PET dataset and thereby further optimize the region of interest and the thus defined volume, or to select a plurality of different examination volumes at one and the same time, which volumes will then be analyzed in subsequent examinations.

FIG. 1 shows a known apparatus 1 for superposed MR and PET imaging. The apparatus 1 includes a known MR tube 2. The MR tube 2 defines a longitudinal direction z which extends orthogonally with respect to the drawing plane of FIG. 1.

As is shown in FIG. 1, a plurality of PET detection units 3 which are arranged in pairs opposite one another about the longitudinal direction z are arranged coaxially within the MR tube 2. The PET detection units 3 preferably consist of an APD photodiode array 5 having an upstream array of LSO crystals 4 and an electric amplifier circuit (AMP) 6. Embodiments of the invention are not, however, limited to the PET detection units 3 having the APD photodiode array 5 and the upstream array of LSO crystals; rather, other types of photodiodes, crystals and apparatuses can equally well be used for detection purposes.

The image processing for superposed MR and PET imaging is carried out by way of a computer 7.

The MR tube 2 defines a cylindrical first field of view along its longitudinal direction z. The multiplicity of PET detection units 3 defines a cylindrical second field of view along the longitudinal direction z. According to an embodiment of the invention the second field of view of the PET detection units 3 essentially corresponds to the first field of view of the MR tube 2. This is realized by a corresponding adjustment of the arrangement density of the PET detection units 3 along the longitudinal direction z.

FIG. 2 schematically shows a section through an MR device 201. The device includes a tubular enclosure 203 having a patient opening 205 in the center. For examination purposes a patient examination couch 207 can be introduced into the patient opening 205. Only sections of the patient examination couch 207 are shown here. Arranged within the enclosure is an annular magnet 209. Arranged inside the magnet 209 is a gradient coil 211. Arranged inside the gradient coil 211 is a carrier tube 213. Recesses 215 into which the PET detectors 217 are inserted are located on the carrier tube 213. As shown in FIG. 3, the carrier tube 213 includes first and second portions 213a and 213b. The recesses 215 are between the first and second portions 213a and 213b. Located at the end of the carrier tube 213 are signal processing units 219 which are connected via electric leads 221 to the PET detectors 217.

A way of cooling the PET detectors 217 can also be provided (for reasons of clarity the cooling device is not shown in the figure). Cooling pipes could be arranged close to the signal processing units 219. Cooling pipes would be arranged, for example, parallel to the electric leads 221.

The carrier tube 213 also includes the electronics of the excitation coil (not shown here) which is typical of an MR device. Implementing an integrated excitation coil inside the carrier tube 213 for the PET detectors 217 provides in particular the advantage of a compact design.

Arranged between the carrier tube 213 and the gradient coil 211 are a plurality of bearings 222. A plurality of bearings 222 can be provided along the circumference of the carrier tube 213. The bearings can be embodied for example as sliding bearings or roller bearings. Other bearing types are also possible. The carrier tube 213 is not fixedly connected to the gradient coil 211 and also not fixedly connected to the enclosure 203 so that it can be displaced relative to the gradient coil 211 in the horizontal direction. In order to maintain the position of the carrier tube 213 a supporting element 225 is provided which is connected to a ring 227. The ring 227 is in turn connected to the carrier tube 213 such that the carrier tube 213 is supported by way of the supporting element 225. At its lower end the supporting element 225 includes a sliding unit 229 which is movable in a sliding rail 231 in the horizontal direction. The sliding rail 231, the sliding unit 229 and the ring 227 are arranged inside the enclosure 203.

FIG. 3 shows the MR device 201 in its opened form. The enclosure 203 is implemented in two parts. A first enclosure part 203a contains the magnet 209 and the gradient coil 211. A second enclosure part 203b is removable and is shown here in its removed state. After the second enclosure part 203b is removed it is possible to withdraw the carrier tube 213 from the gradient coil 211 in the horizontal direction. In the process the bearings 222 and the sliding unit 229 are positioned at an end 232 exiting the MR device 201 and serve therein to guide the carrier tube 213 and to facilitate its displacement. An extension 233 can be mounted onto the sliding rail 231, which extension 233 accommodates the sliding unit 229 as soon as the latter exits the sliding rail 231.

The carrier tube 213 can be withdrawn so far from the enclosure part 203a that access to the PET detectors 217 is made possible. This enables maintenance activities to be carried out on the PET detectors 217, the electric leads 221 and the signal processing units 219. Replacement of components is also possible. For clarification purposes a PET detector 217', an electric lead 221' and a signal processing unit 219' are shown in the removed state.

The bearings 222 and the sliding unit 229 in conjunction with the sliding rail 231 and the extension 233 serve to guide the carrier tube 213. Following a displacement of the carrier tube 213 an exact return to the home position is necessary, since the position of the carrier tube 213 inside the MR device 201 is important.

An advantageous aspect of the example embodiments of the invention is that only the PET detector 217 requiring maintenance or replacement has to be separated from its electrical and mechanical connections. Faster maintenance is possible as a result and the risk of errors is reduced. Owing to the recesses 215 used the relative position of the PET detectors 217 relative to one another is maintained even in the case of a replacement. Complicated and time-consuming calibrations can largely be avoided as a result.

As an alternative to the sliding rail 231 with the corresponding sliding unit 229 a roller can also be provided on the supporting element 225. In this case the carrier tube 213 could be guided by way of the bearings 222 in such a way as to prevent a twisting of the carrier tube 213. Other types of supporting elements 225 are also conceivable.

Figure 4:
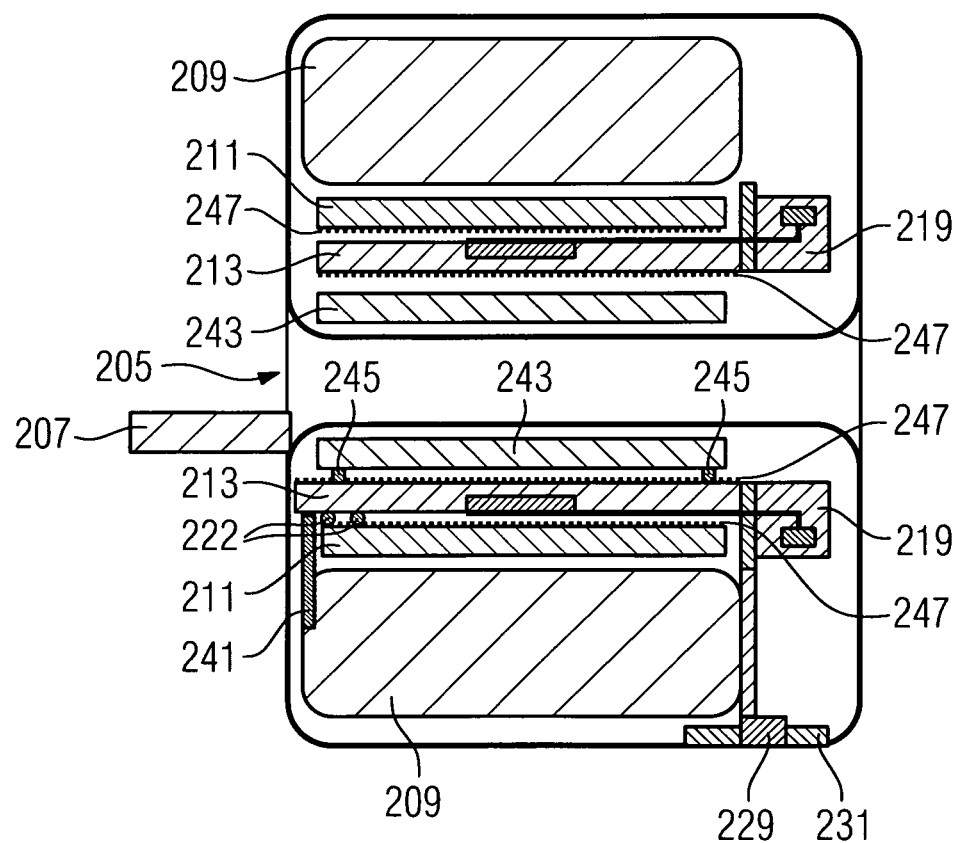
FIG. 4 shows an alternative embodiment variant of the invention.

An alternative embodiment variant of the invention is shown in FIG. 4. In this case the previously permanently installed bearings 222 are implemented as removable. The bearings 222 can be removed after the carrier tube 213 has been inserted into the gradient coil 211. The supporting effect of the bearings 222 in relation to the carrier tube 213 is implemented in this embodiment by way of a supporting element 241. This is secured to the magnet 209 and supports the carrier tube 213 against the magnet 209 in the event that the bearings 222 are removed. This has the advantage that no direct physical contact between the gradient coil 211 and the carrier tube 213 is necessary in order to support the carrier tube 213. Vibrations generated by the gradient coil 211 during operation are therefore transmitted only via the air through the gap between the gradient coil 211 and the carrier tube 213, which is to say only to a limited degree.

With the bearings 222 installed, the carrier tube 213 can be withdrawn analogously to the example embodiment shown in FIGS. 2 and 3. The connection of the carrier tube 213 to the supporting element 241 is detachable for that purpose.

In the example embodiment shown, a separate body coil 243 is provided which is arranged inside the carrier tube 213. The coil is supported on the carrier tube by way of further supporting elements 245. An HF shield 247 is provided in each case inside the gradient coil 211 and the carrier tube 213. Owing to the body coil 243 being supported on the carrier tube 213 and the HF shield 247 being installed on the carrier tube 213, the position of the body coil 243 relative to its shield 247 does not change after a maintenance intervention on the PET detectors 217, with the result that no new calibration is required.

This implementation of the body coil 243 can also be realized with the embodiment variant shown in FIGS. 2 and 3. Similarly, the integrated implementation of the body coil inside the carrier tube 213 shown there can be used with the implementation of the support by way of the supporting element 241 shown here.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed:

1. A magnetic resonance and positron emission tomography (PET) imaging device, comprising:
a magnet defining a bore;
a PET unit within the bore, the PET unit configured to acquire positron emission tomography data; and
a gradient coil within the bore, the PET unit including a carrier tube on which at least one PET detector is arranged, the carrier tube being arranged inside the gradient coil, being displaceably mounted to access the at least one PET detector by displacement, and the carrier tube having a surface area, a portion of the surface area being indented to form at least one recess for accommodating the at least one PET detector, a thickness of the carrier tube at the at least one recess being less than a thickness at first and second portions of the carrier tube, the at least one recess being between the first and second portions of the carrier tube.

2. The magnetic resonance device as claimed in claim 1, wherein at least one sliding bearing is arranged between the gradient coil and the carrier tube.

3. The magnetic resonance device as claimed in claim 1, wherein at least one roller bearing is arranged between the gradient coil and the carrier tube.

4. The magnetic resonance device as claimed in claim 1, further including a sliding rail, connected by way of a supporting element to an end of the carrier tube configured to exit the magnetic resonance device during displacement of the carrier tube.

5. The magnetic resonance device as claimed in claim 4, wherein the sliding rail is configured to accommodate an extension into which the supporting element is transferable during displacement of the carrier tube.

6. The magnetic resonance device as claimed in claim 1, further including at least one signal processing unit for PET signals which is disposed on the carrier tube and arranged at the end of the carrier tube configured to exit the magnetic resonance device during displacement of the carrier tube.

7. The magnetic resonance device as claimed in claim 1, further including an enclosure comprising at least two enclosure parts, wherein the enclosure parts are detachably connected to each other and embodied in such a way that a displacement of the carrier tube is made possible when a first enclosure part is removed.

8. The magnetic resonance device as claimed in claim 1, wherein an excitation coil is inside the carrier tube such that it is displaceable with the carrier tube.

9. The magnetic resonance device as claimed in claim 1, wherein a shield for high-frequency radiation is arranged on the inside of the carrier tube in such a way that it is displaceable together with the carrier tube.

10. The magnetic resonance device as claimed in claim 2, further including a sliding rail, connected by way of a supporting element to an end of the carrier tube configured to exit the magnetic resonance device during displacement of the carrier tube.

11. The magnetic resonance device as claimed in claim 10, wherein the sliding rail is configured to accommodate an extension into which the supporting element is transferable during displacement of the carrier tube.

12. The magnetic resonance device as claimed in claim 3, further including a sliding rail, connected by way of a supporting element to an end of the carrier tube configured to exit the magnetic resonance device during displacement of the carrier tube.

13. The magnetic resonance device as claimed in claim 12, wherein the sliding rail is configured to accommodate an extension into which the supporting element is transferable during displacement of the carrier tube.

* * * * *